United States Patent [19]
Boos et al.

[11] Patent Number: 5,170,791
[45] Date of Patent: Dec. 15, 1992

[54] METHOD AND APPARATUS FOR CALCULATING THE FETAL HEART RATE

[75] Inventors: Andreas Boos, Bondorf; Martin Schraag, Sindelfingen, both of Fed. Rep. of Germany

[73] Assignee: Hewlett-Packard Company, Palo Alto, Calif.

[21] Appl. No.: 676,886

[22] Filed: Mar. 28, 1991

[51] Int. Cl.$^5$ ............................................. A61B 8/00
[52] U.S. Cl. .................. 128/661.07; 128/696; 128/698; 128/661.04
[58] Field of Search ................. 128/661.07, 696, 698, 128/709, 703, 661.08, 661.09, 661.04; 73/861.25

[56] References Cited

U.S. PATENT DOCUMENTS

| | | | |
|---|---|---|---|
| 3,982,528 | 9/1976 | Phillipps | 128/661.07 |
| 3,991,365 | 11/1976 | Takeuchi | 128/661.07 |
| 4,211,237 | 7/1980 | Nagel | 128/698 |
| 4,456,959 | 6/1984 | Hirano et al. | 128/698 |
| 4,537,200 | 8/1985 | Widrow | 128/696 |
| 4,569,356 | 2/1986 | Kyozuka | 128/661.07 |

Primary Examiner—Kyle L. Howell
Assistant Examiner—George Manuel

[57] ABSTRACT

Determining the fetal heart rate comprises irradiating an ultrasound beam in the direction of the fetal heart. The moving parts of the fetal heart cause a Doppler shift which is used to determine the fetal heart rate via an autocorrelation function. Moving parts of the fetal heart with different velocities and Doppler shifts originating from other physiological sources generate secondary maxima in the autocorrelation function, so that an accurate heart rate determination becomes nearly impossible. This problem is overcome by parallel processing of the demodulated ultrasound signal in various pass-bands, for which purpose the signal is fed to filters (28, 30) of different frequency characteristics. The output of the pass band with the better result is used for fetal heart rate circulation.

33 Claims, 5 Drawing Sheets

METHOD AND APPARATUS FOR CALCULATING THE FETAL HEART RATE

FIELD OF THE INVENTION

The present invention generally relates to methods and apparatuses for determining the heart rate of a subject, and particularly relates to methods and apparatuses for determining the beat-to-beat heart rate of a fetus.

BACKGROUND OF THE INVENTION

Fetal monitoring (i.e., monitoring of the fetal condition during gestation and at birth) usually comprises monitoring of the uterus activity (toco) and of the fetal beat-to-beat heart rate (FHR). The fetal heart rate is the more important of these parameters, as it provides an indication of whether the fetus is sufficiently supplied with oxygen. Of course, both parameters may also be used for further diagnostic statements. In particular, the relation between fetal heart rate and labor is used to evaluate the fetal condition. The present invention relates to the calculation of the fetal heart rate. This heart rate is preferably calculated from beat to beat; i.e., the heart rate is calculated after each beat by means of the time interval to the preceding beat. The beat-to-beat heart rate is most meaningful for diagnostic purposes; however it is also possible to calculate the fetal heart rate over longer time intervals or to average the beat-to-beat heart rate.

To obtain a signal indicative of the fetal heart rate, a so-called fetal scalp electrode may be applied to the fetal skin. These electrodes are usually spiral electrodes which are screwed into the fetal epidermis. The electrodes provide very accurate measurements due to the excellent signal quality. Unfortunately, this so-called internal or direct measurement may only be used after rupture of the membranes. Prior to that point in time (in particular, during gestation), indirect methods must be used. The indirect measurements are performed abdominally, e.g., by listening to the fetal heart sound or by measuring the Doppler shift of an ultrasound signal reflected by the moving fetal heart.

The ultrasound technique is the most common one. According to this technique, an ultrasound transducer is placed externally on the pregnant woman's abdomen. Its orientation is selected such that the emitted ultrasound waves reflect off the fetal heart. The reflected ultrasound wave is received either by the same or by another ultrasound transducer. The Doppler shift of the reflected ultrasound wave is directly related to the speed of the moving parts of the heart, e.g., the heart valves and the heart walls.

To extract the Doppler component from the received ultrasound signal, the received ultrasound signal is demodulated. Further processing depends on the specific application. For example, the Doppler signal may be fed to an audio amplifier, thus giving an acoustic indication of the heart beat; however, in order to generate a digital representation of the heart rate, more sophisticated techniques must be used. One such sophisticated technique which is commonly used in fetal monitors is the autocorrelation technique. According to this technique, the Doppler signal or the envelope of the Doppler signal is correlated with itself, thus providing significant peaks in time intervals which correspond to periodic components of the Doppler signal that are due to the fetal heart beat. Such techniques are necessary as the received ultrasound signals contain noise originating from various physiological sources, such as the maternal aorta, movement of the fetus as a whole, and the like.

In prior art devices, a peak trigger device or an equivalent circuit detects the peaks in the autocorrelation function. The beat-to-beat heart rate, computed as the inverse of the time interval between two successive heart beats, is then available for further processing, display and/or recordation.

Even the highly sophisticated autocorrelation technique is not always reliable. In particular, the autocorrelation function may contain several maxima, so that it becomes difficult to distinguish between significant maxima relating to a heart beat and secondary maxima. Moreover, the autocorrelation function may be distorted so that it is impossible to identify peaks at all. In these cases the calculated fetal heart rate may be inaccurate, or it may even be impossible to obtain a heart rate signal at all.

Figure 1:
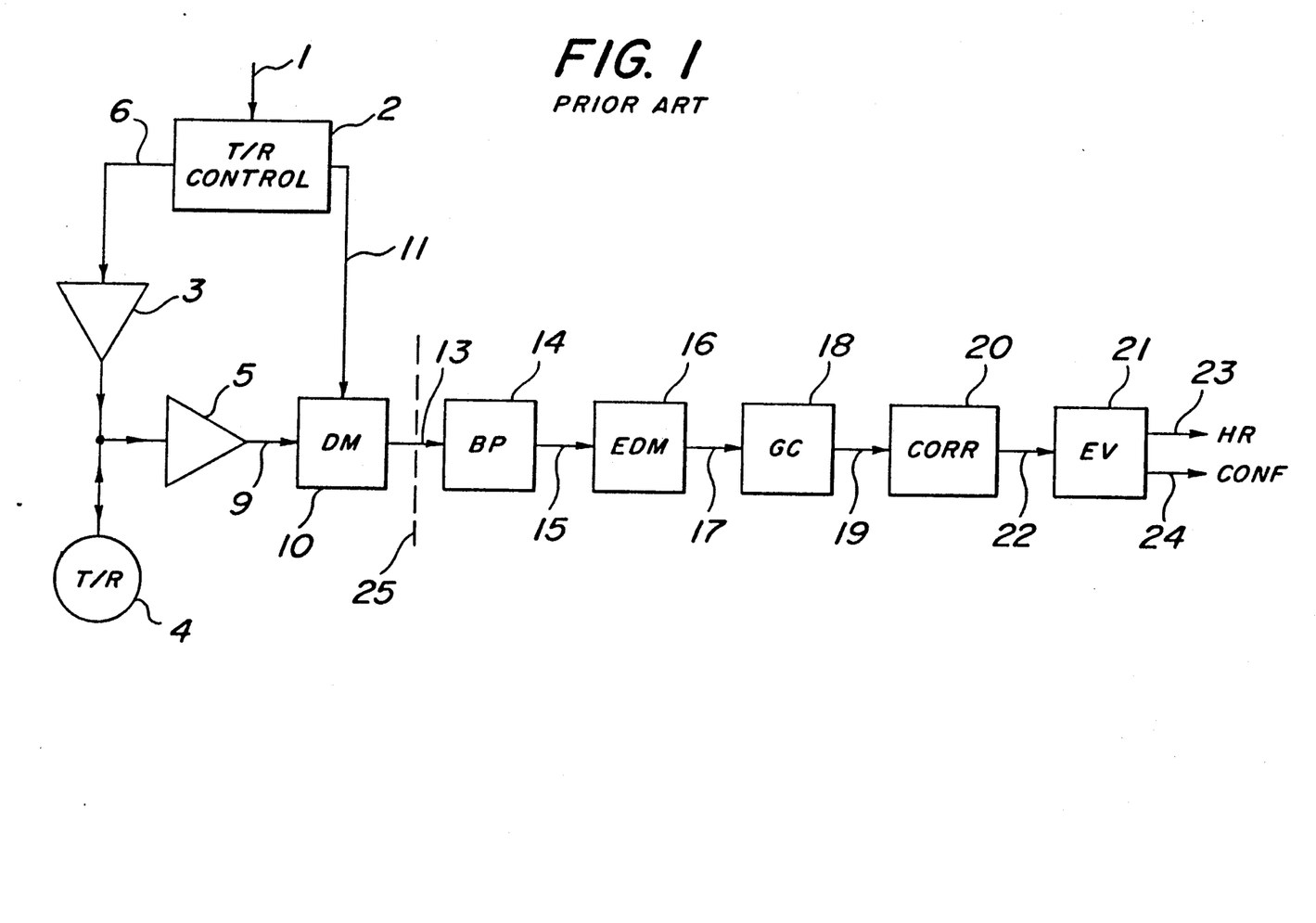
FIG. 1 is a block diagram of the ultrasound processing path in a prior art fetal monitor.
Figure 2A:
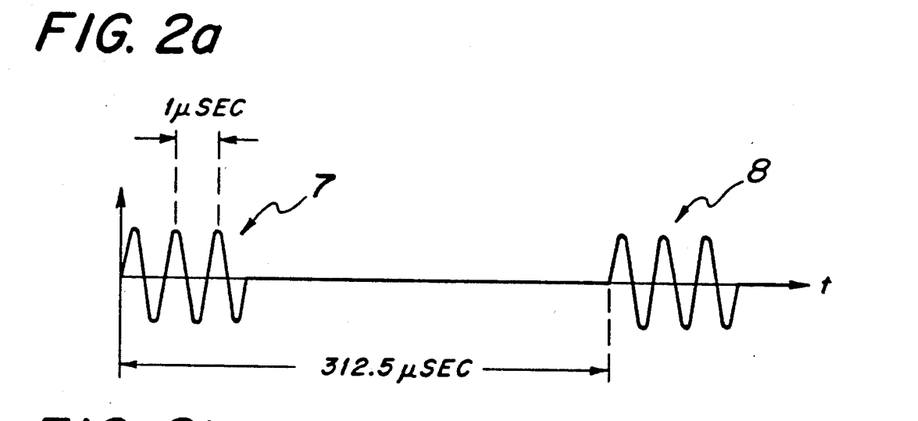
FIGS. 2a and 2b depict ultrasound waveforms in connection with the block diagram of FIG. 1.

In the prior art circuit depicted in FIG. 1, a 1 MHz signal is fed via line 1 to a transmission/reception control circuit 2. The signal is then fed via a high-frequency amplifier 3 to a transducer 4. This transducer comprises piezo-electric crystals which are capable of transmitting and receiving ultrasound waves. In clinical applications, the ultrasound transducer 4 is placed on the maternal abdomen such that the ultrasound waves are emitted in the general direction of the fetal heart. The ultrasound waves reflected by the fetal heart and other fetal tissue are then received by ultrasound transducer 4 and fed to a second high-frequency amplifier 5. The ultrasound waves are irradiated into the maternal and fetal tissue as burst waves, i.e., "packages" of high-frequency (1 MHz) waves. The repetition rate of the bursts is 3.2 kHz. This is illustrated in FIG. 2a. The signal depicted in FIG. 2a is the signal which is fed from transmission/reception control circuit 2 to amplifier 3 via line 6.

The emitted ultrasound signal consists of bursts 7, 8, etc. The bursts are emitted in time intervals of 312.5 μsec, which corresponds to a repetition rate of 3.2 kHz. The frequency of the waves within the bursts is 1 MHz, i.e., the time interval between their respective amplitudes is 1 μsec, as illustrated in FIG. 2a.

Figure 2B:
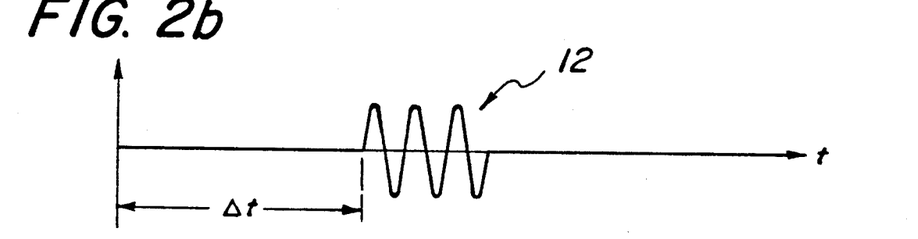

The signal generated by high-frequency amplifier 5 is then fed via line 9 to a demodulator circuit 10 ("DM"). Demodulator circuit 10 also receives a control signal from transmission/reception control circuit 2 on line 11. The control signal on line 11 is also depicted in FIG. 2b. Burst 12 of this signal is shifted in time with respect to burst 7 in FIG. 2a. The time shift is labelled as Δt in FIG. 2b. This time shift takes into account the propagation delay between the onset of the emitted ultrasound burst and the time when the reflected ultrasound wave is received. Δt may be varied in accordance with the distance between the ultrasound transducer 4 and the fetal heart.

Demodulator 10 produces a signal which is indicative of the Doppler shift of the received ultrasound signal with respect to the transmitted signal. The Doppler shift is caused by the moving parts of the fetal heart, in particular the heart walls and the heart valves.

The Doppler signal produced by demodulator 10 is fed, via line 13, to a bandpass filter with a pass band between 100 and 500 Hz to remove unwanted components in the Doppler signal. The signal is then fed, via line 15, to an envelope demodulator 16 ("EDM"). The envelope demodulator generates the envelope of the peaks of the Doppler signal, as the signal of interest is primarily the intensity of the Doppler signal.

Line 17 connects the output of envelope demodulator 16 with a gain control circuit 18. After having passed the gain control circuit, the signal is fed via line 19 to an autocorrelation circuit 20. Autocorrelator circuit 20 correlates the signal received on line 19 with itself. A major feature of the autocorrelation function is that periodic components in the incoming signal are amplified, whereas non-periodic or stochastic signals are widely suppressed; therefore, autocorrelation is ideally suited to amplify the periodic components, in contrast to non-periodic signals, e.g., signals caused by fetal movement, maternal tissue or the like.

Figure 3:
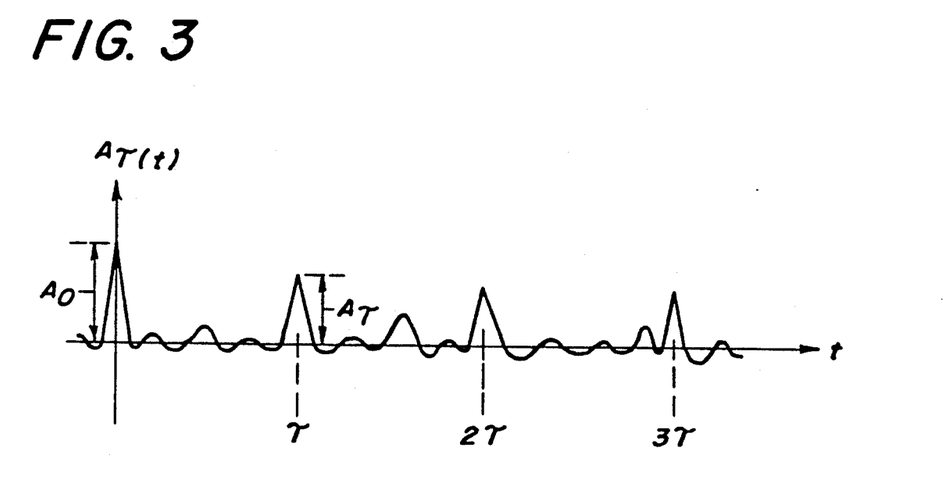
FIG. 3 depicts an autocorrelation function $A_{r(t)}$.

The basic equation for calculating the autocorrelation function is $$A_{r(t)} = \int_{-\infty}^{+\infty} r(t)r(t - \tau)d\tau \quad (1)$$

wherein r(t) is the incoming (autocorrelated) signal. FIG. 3 depicts a typical autocorrelation function $A_{r(t)}$ over time. It will be noted that the amplitude of the autocorrelation function is at its maximum $A_0$ at t=0. Further maximums occur at $t=\tau$, $t=2\tau$, $t=3\tau$, and so on. $\tau$ in this notation represents the time between one significant peak of the autocorrelation function and the next significant peak. The significant peaks in the autocorrelation function relate to fetal heart beats and have an approximately equidistant separation between successive peaks. Their amplitude is labelled as $A_\tau$ in FIG. 3. It should be noted that the above equation describes an ideal autocorrelator. It will be understood that a real autocorrelator approximates this function, e.g., by taking the sum instead of the integral, and by finite integration limits instead of the infinite limits given above.

The autocorrelation function generated by autocorrelator 20 is used to calculate the fetal heart rate. This is done by evaluation circuit 21 to which the output of autocorrelator 20 is fed via line 22. In fetal monitoring applications, the beat-to-beat heart rate has the highest diagnostic value. It is calculated as the inverse of the time interval between two adjacent peaks in the autocorrelogram. It should be noted, however, that there are other ways to calculate the heart rate, e.g., computing it over a longer time interval, averaging the time intervals or averaging the heart rate.

The generated heart rate ("HR") is fed via line 23 to further circuitry, e.g., a display, a recorder, a central station or the like.

Evaluation circuit 21 also provides a liability coefficient "CONF" via line 24. The reliability coefficient indicates the quality of the autocorrelation function and therefore the quality of the received ultrasound wave. This is important for the physician or the nurse, as a poor-quality signal may result in an incorrect heart rate. Such may happen, e.g., if the ultrasound beam is not sufficiently focussed on the fetal heart. A low reliability coefficient is therefore an indication that the ultrasound transducer should be readjusted. One way of indicating the reliability or quality of the signal is to use lamps or light-emitting diodes of different colors (e.g. red, yellow and green).

The reliability coefficient may be calculated in different ways. Referring to FIG. 3, a preferred solution is to calculate the ratio between the amplitude $A_\tau$ of a peak relating to a heart beat and the amplitude $A_0$ of the autocorrelation function when the signal is correlated with itself. The coefficient $$\frac{A_\tau}{A_0} \quad (2)$$

is a quite good estimation of the quality of the signal. The reliability coefficient may also be calculated or determined in a different manner, e.g., by taking the absolute amplitude $A_\tau$, by determining the area under a significant peak (by integration), or the like.

The inventors of the present invention have found that the deficiencies of the prior art autocorrelation technique, and therefore the deficiencies of the fetal heart rate obtained with prior art monitors using this technique, are primarily caused by two effects: First, the Doppler shift of the reflected ultrasound signal originates from various moving boundary surfaces in the fetal heart. The corresponding components of the Doppler signal change their frequency as well as their amplitude independent of each other if the angle of the incident ultrasound wave is only slightly changed. This results in a very complex Doppler signal (or envelope signal) which changes over time. An autocorrelation function based upon this signal contains not only the main maxima (or significant peaks) corresponding to heart beats, but also various secondary peaks varying over time. These secondary maxima or peaks affect the evaluation of the autocorrelogram and therefore also affect the determination of the beat-to-beat heart rate. The second problem originates from the fact that not all components of the received ultrasound signal originate from the fetal heart. Such components may be superimposed on the reflections of the fetal heart and may even cover them. Determination of the fetal heart rate by means of an autocorrelation technique may deliver inaccurate results if such happens.

It is therefore a major objective of the present invention to provide a method and apparatus which generate more reliable heart rate signals, particularly, more reliable fetal heart rate signals.

SUMMARY OF THE INVENTION

The present invention provides a method for determining a heart rate from a signal having a plurality of frequency components at least one of which is indicative of heart beats. The method comprises the steps of processing the signal to produce first and second signals having different frequency characteristics, identifying which of the first and second signals contains the more reliable indication of the heart rate, and generating a heart rate signal on the basis of the signal identified as containing the more reliable indication.

In a preferred embodiment of the invention at least one of the first and second signals is indicative of an autocorrelation function. In this case, the method may further comprise detecting at least two peaks in the autocorrelation function and calculating the heart rate on the basis of the time interval between the peaks. The heart rate is most preferably calculated from beat to beat as the inverse of the time interval between the peaks.

In another embodiment, the method comprises computing a reliability coefficient as a function of the ratio of the amplitude of the autocorrelation function at two peaks. Alternatively, the reliability coefficient may be computed as a function of the amplitude of the autocorrelation function at a peak.

In another embodiment, the method comprises computing an autocorrelation function on the basis of at least one of the first and second signals, computing a cross-correlation function on the basis of at least the autocorrelation function, and identifying, on the basis of at least the cross-correlation function, which of the first and second signals contains the more reliable indication of the heart rate.

In yet another embodiment, the method comprises computing a reliability coefficient for the first and second signals and selecting the signal with the higher reliability coefficient. The selection is performed in discrete steps in this embodiment. E.g., the selection may be performed when a predefined number of heartbeats have been detected or at predefined time intervals.

In yet another embodiment, the method comprises computing a reliability coefficient for each of the first and second signals, and selecting the signal with the higher reliability coefficient when the reliability coefficients bear a predefined relation to each other.

In the most preferred embodiment the first and second signals are produced by feeding a demodulated ultrasound signal to first and second filters, the first filter having low pass characteristics and the second filter having high pass characteristics. The first filter preferably will have an upper cutoff frequency approximately equal to the lower cutoff frequency of the second filter. The upper and lower cutoff frequencies are preferably around 180 Hz.

The present invention also encompasses apparatuses for carrying out the methods recited above.

In addition, the present invention encompasses apparatuses (and corresponding methods) for monitoring a periodically-moving object, the apparatus having means for transmitting an ultrasound signal towards moving parts of the object and receiving a reflected signal. The apparatus is characterized by means for filtering the complex signal to output filtered signals with different frequency characteristics; means for enhancing periodic components of each filtered signal and suppressing non-periodic components of each filtered signal; means for assessing the quality of each enhanced signal; means for selecting a desired enhanced signal with the highest quality; and means for calculating the rate of the periodic movement based upon the enhanced signal with the highest quality.

DETAILED DESCRIPTION OF THE PREFERRED EMBODIMENTS

In a preferred embodiment of the invention, a demodulated ultrasound signal is fed to at least two filters, typically a low pass filter and a high pass filter (however, designs with more than two filters, e.g., a low pass filter, a band pass filter and a high pass filter, are within the scope of the invention as well). The output signals of these two or more filters are then processed substantially in parallel, namely by performing an autocorrelation on each of the filtered signals and determining a reliability coefficient relating to each of the autocorrelation functions. Finally, logic or other circuitry selects the autocorrelation function with the higher reliability coefficient, i.e., the "better" autocorrelation function. This autocorrelation function is then processed as usual, i.e., the peaks in the autocorrelation function are detected and used to calculate the fetal heart rate. All the individual method steps and/or components used to process the autocorrelation signal may be identical to prior art monitors. The major contribution of the present invention is therefore that the demodulated ultrasound signal is processed in parallel by two or more paths of different frequency pass-bands, that an autocorrelation is performed on each of them, that the quality of each autocorrelation function is assessed and that the one with the highest degree of reliability or quality is selected.

The invention is based on the following considerations: The fetal heart comprises several moving boundary surfaces or layers which move with different velocities. This results in Doppler signals of different frequencies, as the velocity of the moving object is proportional to the Doppler frequency. For example, heart valves move faster than heart walls; therefore heart valves primarily cause Doppler signals of high frequency, whereas heart walls cause Doppler signals of low frequency.

If the demodulated Doppler signal (or its envelope, or another function related to it) is split into various frequency pass-bands, a signal which contains only one (or a few) frequency component(s) is obtained. In the above-mentioned example with a low pass filter and a high pass filter, the major components contained in the Doppler signal and originating from the heart valves will therefore be contained in the high-frequency path, whereas the signals resulting from the heart walls will be contained in the low-frequency path. This measure reduces the complexity of the Doppler signal, or its envelope signal, which in turn reduces the complexity of the autocorrelation function. The autocorrelation function will therefore contain less peaks, so that the significant peaks relating to heart beats will be easier to identify.

Another observation is that superimposed signals originating from a single moving boundary (e.g., the fetal arm) produce a Doppler signal which has a very small frequency band. If the frequency band of the instrument is split into multiple partial bands, the frequency components corresponding to this superimposed noise will only appear in one of those partial bands. These other partial frequency bands will therefore be unaffected by the superimposed noise and may be used for accurate heart rate determination.

It is understood that the selection between the various autocorrelation functions provided may be performed either continuously or in discrete steps; however the selection in discrete steps is the preferred approach. In particular, it is an object of the invention to avoid switching between the autocorrelation functions too frequently, as this could cause jitter in the selected autocorrelation function and, therefore, cause jitter in the heart beat (or heart rate) signal. According to an advantageous embodiment of the invention, this object is solved in that the selection of an autocorrelation function is performed when either a predefined number of fetal heart beats have been observed, or when a predefined time period has expired. Another preferred solution provides the selection of an autocorrelation function when the difference between or the quotient of the reliability coefficients exceeds or falls below a predefined limit, which may be a fixed or adaptive limit. This latter feature implements a "hysteresis" function.

As indicated above, two, three or even more filters and corresponding autocorrelation paths may be used to improve operation of the fetal monitor. As more filters are used, the related frequency pass-bands become smaller. This increases the probability that an autocorrelation function of high quality can be found in at least one of the corresponding paths. Note however that the bandwidth of a single path should not be made too small, as signals originating from a common physiological source would be split into different pass-bands. Furthermore, it should be noted that as more filters and autocorrelators are used, more hardware and/or software will be required.

Tests have shown that in many practical cases two filters with the associated processing are sufficient to obtain a significant improvement of signal quality. Although it is a compromise between resolution of the pass-bands and technical efforts (i.e., engineering time), the embodiment with two filters provide excellent results. In this embodiment one filter has low pass characteristics and the other filter high pass characteristics. The cutoff frequencies of the two filters are approximately equal, so that no frequency components are lost, but also no frequency components are processed twice. Tests have shown that a suitable cutoff frequency for the low pass and the high pass filters is 180 Hz.

In a further advantageous embodiment, the ultrasound signals are high-frequency ultrasound bursts. By selecting a certain reception period or interval, it becomes possible to receive only signals resulting from a certain depth in the fetal tissue, i.e., to perform "depth selection."

Figure 4:
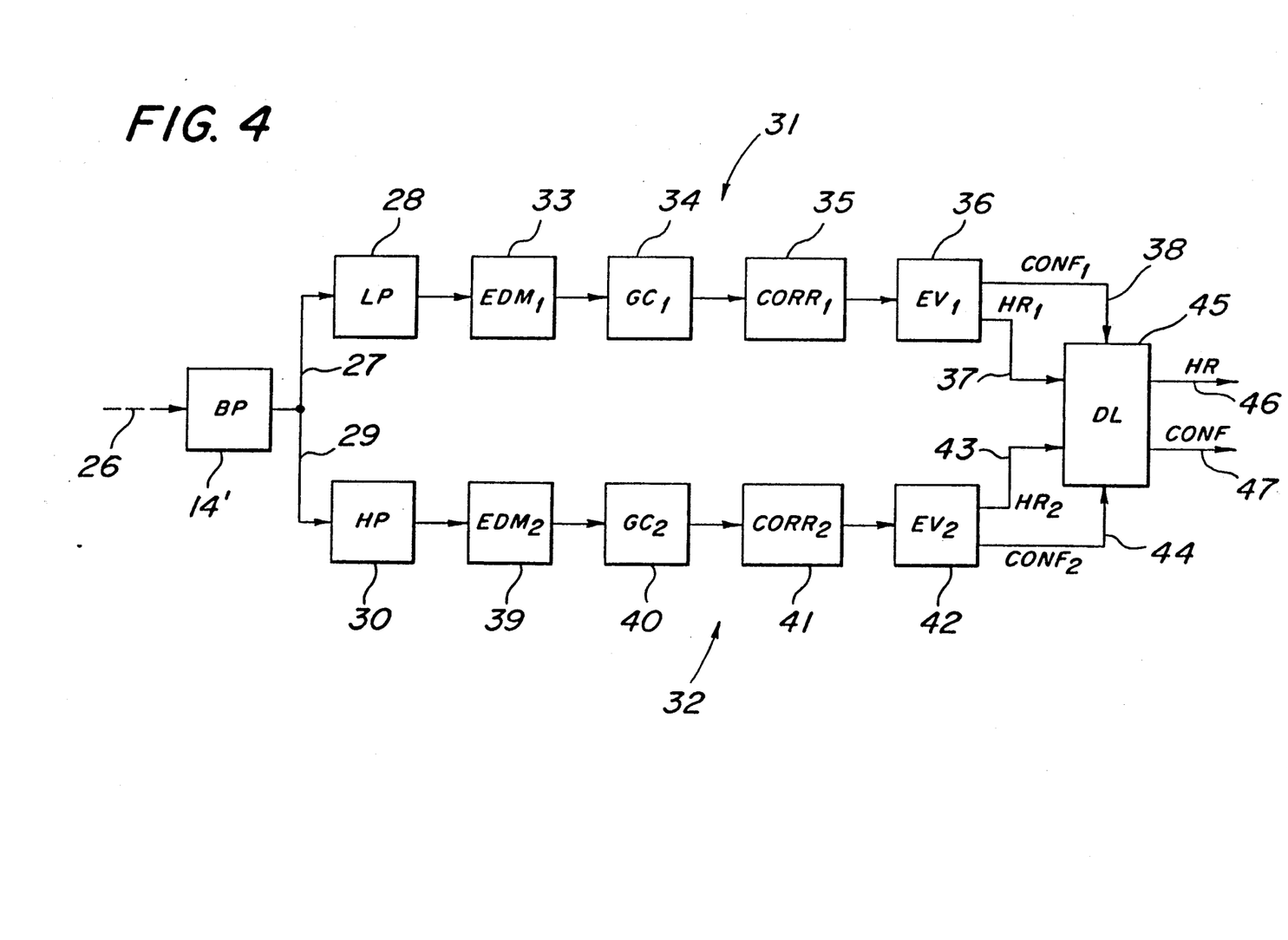
FIG. 4 is a block diagram of the processing path of the ultrasound signals according to the present invention.

FIG. 4 depicts a block diagram of one embodiment of the invention. The individual components for transmitting, receiving and demodulating the ultrasound signal are identical to the prior art circuit (but of course the individual components are combined in a novel way); therefore, the components left of dashed line 25 (in FIG. 1) are not depicted in FIG. 4.

In FIG. 4, the demodulator output is fed (line 26) to band pass 14' (which is identical to band pass 14 in FIG. 1). The output of band pass 14' is fed (line 27) to a low pass filter ("LP") 28 with a cutoff frequency of 180 Hz; i.e., low pass filter 28 suppresses all frequencies beyond 180 Hz. Likewise, the output of band pass 14' is fed (line 29) to a high pass filter ("HP") 30 which has a cutoff frequency of 180 Hz (but, in contrast to the low pass filter, suppresses frequencies below 180 Hz). The outputs of the two filters 28, 30 are processed in a similar manner in two parallel signal paths 31, 32. The output of low pass filter 28 is fed to a first envelope demodulator ("EDM$_1$") 33, then to a first gain control circuit ("GC$_1$") 34, to a first autocorrelator ("CORR$_1$") 35 and to a first evaluation circuit ("EV$_1$") 36. Elements 33-36 correspond to elements 16, 18, 20 and 21 in FIG. 1. First evaluation circuit 36 generates a first heart rate signal HR$_1$ on line 37 and a first reliability coefficient CONF$_1$ on line 38. It should be noted that heart rate signal HR$_1$ and its corresponding reliability coefficient are calculated from a Doppler signal which contains only frequency components below 180 Hz; as the fetal heart walls usually move slower than the fetal heart valves, HR$_1$ primarily originates from the ultrasound waves reflected by the fetal heart walls.

The output of high pass filter 30 is fed through envelope demodulator 39, gain control circuit 40, autocorrelator 41 and evaluation circuit 42. Heart rate signal HR$_2$ (on line 43) primarily represents the movement of the fetal heart valves. Reliability coefficient CONF$_2$ (on line 44) relates to heart rate signal HR$_2$.

Decision logic ("DL") 45 receives the two heart rate signals HR$_1$, HR$_2$ and the two reliability coefficients CONF$_1$ and CONF$_2$. The decision logic circuitry contains means (e.g. a comparator) for comparing the two reliability coefficients CONF$_1$, CONF$_2$. The decision logic feeds the heart rate with the higher reliability coefficient to its output ("HR," line 46). The reliability coefficient "CONF" of heart rate signal HR is also put out through the decision logic onto line 47.

As an example, assume that the ultrasound beam is primarily focussed on the fetal heart valves, and that the signal from the fetal heart walls is distorted. Reliability coefficient CONF$_1$ in this case will be low (due to the poor signal in the low frequency range), whereas the reliability coefficient CONF$_2$ of the high-frequency Doppler component (which has passed high-pass filter 30) will be relatively high. Decision logic circuit 45 determines that $$CONF_1 < CONF_2 \tag{3}$$

It therefore feeds signals HR$_2$ and CONF$_2$ to its output, i.e., $$HR = HR_2 \tag{4a}$$

$$CONF = CONF_2 \tag{4b}$$

The circuitry after decision logic 45 may be the same as in prior art monitors; i.e., heart rate signal HR and reliability coefficient CONF may be processed and displayed, recorded, etc., as usual.

Decision logic circuit 45 may also comprise means for preventing its output channels from being switched between the two heart rates too often. A first solution is to implement a hysteresis function, i.e., to switch the output only if the reliability coefficient of one channel exceeds the reliability coefficient of the other channel by a certain amount. It is also possible to avoid switching the output of decision logic circuit 45 for a certain amount of time, or for a certain number of heart beats. A third solution is to average the respective reliability coefficients. There are other solutions as well. For the sake of completeness, it is noted that evaluation circuits 21 (FIG. 1), 36 and 42 (FIG. 4) also comprise peak triggers which trigger on significant peaks in the autocorrelogram. The trigger level may be constant or adaptive.

Figure 5:
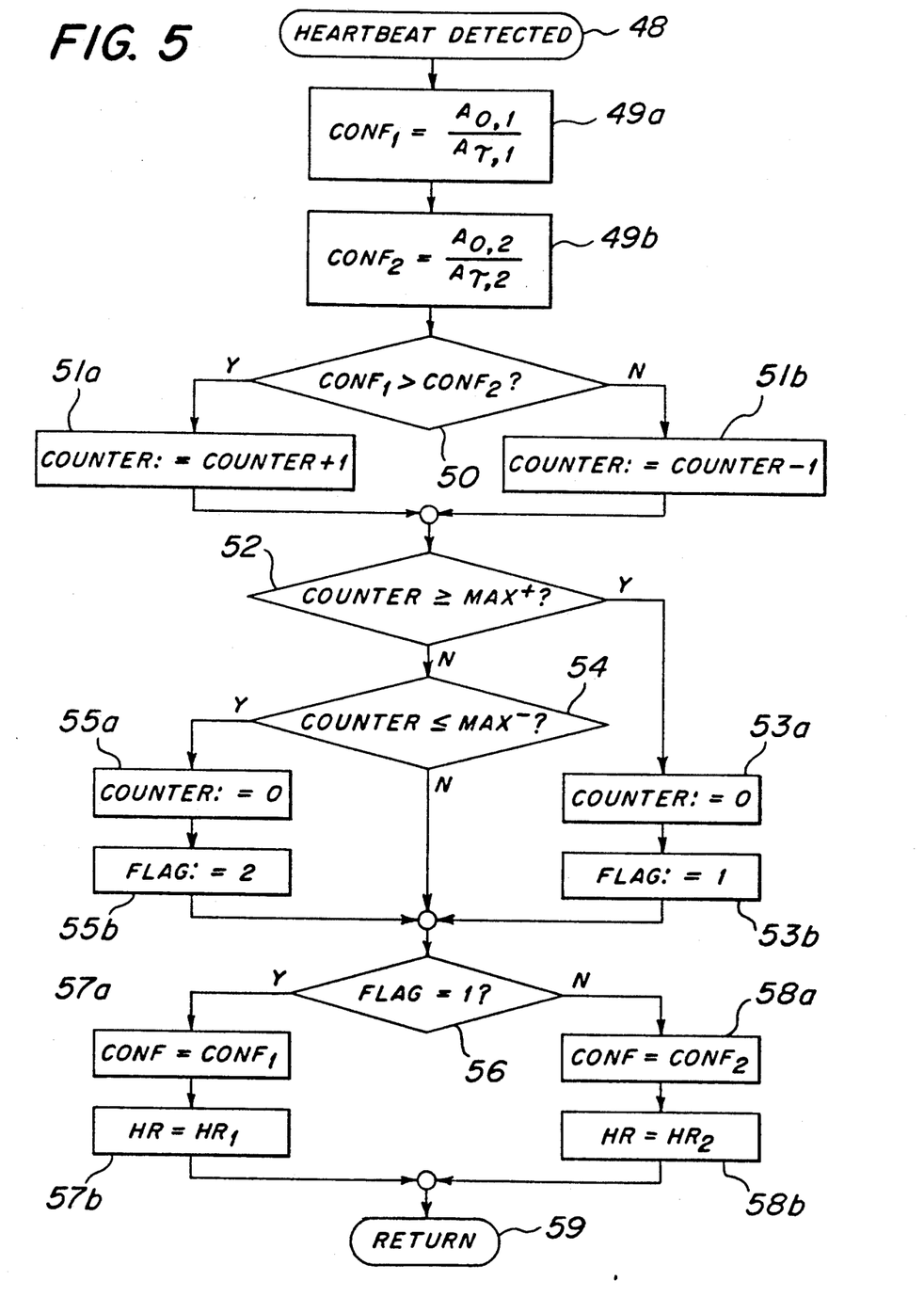
FIG. 5 depicts a flow chart of the basic selection algorithm of the present invention.

FIG. 5 depicts a flow chart of the operation of evaluation circuits 36 and 42 and of the decision logic circuit 45. Once a heart beat has been detected (reference number 48), the decision logic calculates the reliability coefficient of the heart rate based on the low-frequency autocorrelogram, i.e., in accordance with the equation:

$$CONF_1 = \frac{A_{0,1}}{A_{T,1}} \quad (5)$$

(see box 49a). Similarly, the reliability coefficient of the high-frequency-based heart rate is calculated (box 49b). In step 50, the reliability coefficients are compared against each other. If $CONF_1$ is greater than $CONF_2$, i.e., if the low-frequency autocorrelogram exhibits better quality, a counter is increased by 1 (box 51a); otherwise, the counter is decreased by 1 (box 51b).

If the counter has reached or exceeds a positive maximum MAX+ (step 52), it is reset to zero (box 53a), and a flag is set to one (box 53b). On the other hand, if the counter equals or falls below a negative maximum (i.e., a minimum) MAX. (step 54), it is reset (box 55a), but the flag is set to a value of 2 in this case (box 55b). If the counter is between MAX+ and MAX−, operation proceeds directly to step 56.

The purpose of increasing/decreasing and checking the counter is to prevent the decision logic from switching between the heart rate signals $HR_1$ and $HR_2$ too often, i.e., to implement a hysteresis function. In other words, once the decision logic has selected a certain heart rate signal, the other heart rate signal is not selected until a certain number of heart beats has occurred.

In step 56 a test of the flag is made; if it equals 1, this is an indication that the low-frequency autocorrelogram offers better results, and therefore the decision logic renders the low-frequency reliability coefficient $CONF_1$ (box 57a) and the low-frequency based heart rate signal $HR_1$ (box 57b) to a display or recorder (not shown). Otherwise, the reliability coefficient $CONF_2$ and the heart rate signal $HR_2$ derived from the high-frequency autocorrelogram are fed to the output of the decision logic (boxes 58a and 58b). The decision process then stops (reference number 59).

Figure 6:
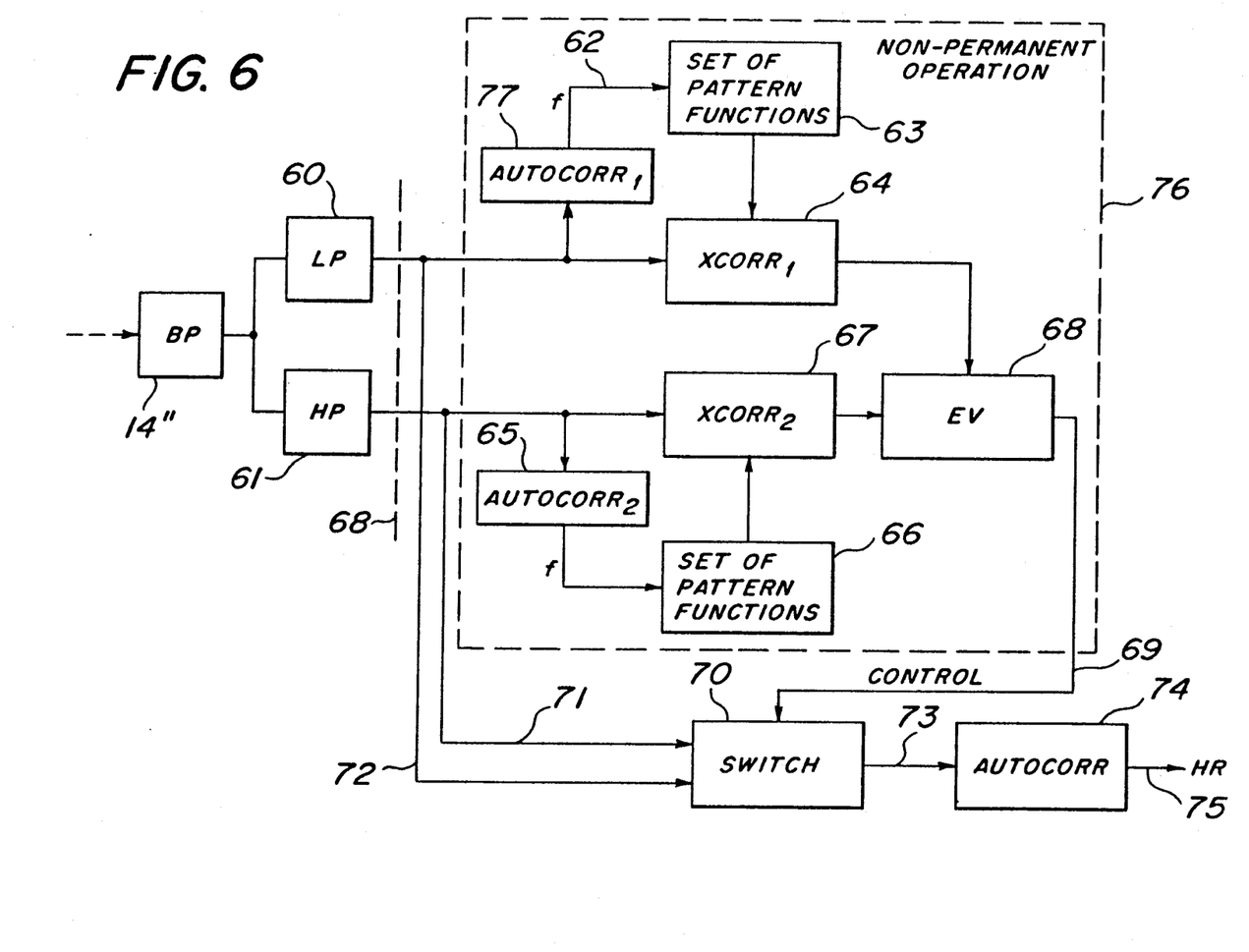
FIG. 6 is a block diagram of an alternative embodiment of the present invention.

FIG. 6 depicts an alternative embodiment of the present invention. In this embodiment the demodulated ultrasound signal is fed to band pass filter 14'' and then to low pass filter 60 and high pass filter 61. The signal generated by low pass filter 60 is then fed to an autocorrelator 77. A peak trigger in the autocorrelator puts the frequency f (or a signal indicative thereof) of the low-frequency components onto line 62. Box 63 contains a set of pattern functions, i.e., of ideal autocorrelation functions, of different frequencies. Frequency f is used to select the pattern function with the same frequency as the low-frequency ultrasound signal. This pattern function is then correlated with the demodulated low-frequency ultrasound signal in cross-correlator 64.

The output of high pass filter 61 is processed in a similar manner with autocorrelator 65, a set of pattern functions 66 and a cross-correlator 67. (It should be noted that the envelope demodulators and the gain control circuits are not depicted in FIG. 6, as indicated by dashed line 68; they are nevertheless part of the preferred embodiment.)

The outputs of cross-correlators 64 and 67 are passed on to an evaluation circuit 68 ("EV") which makes a decision on the quality of the cross-correlograms. A control signal indicating the correlogram of better quality is fed via line 69 to a switch 70, which also receives the demodulated ultrasound signals via lines 71 and 72. Dependent on the status of the control signal on line 69, switch 70 feeds either the low-frequency signal or the high-frequency signal to its output, line 73. The signal on line 73 is then fed to an autocorrelator 74, which is used to generate the heart rate signal HR on line 75.

The circuit depicted in FIG. 6 has the advantage that the autocorrelation is only performed on one signal (box 74). All operations contained in box 76 (surrounded by dashed lines) are executed on a non-permanent or non-periodic basis, i.e., only in certain intervals, and therefore require little processor time. It is evident however that the circuit of FIG. 6 requires considerably greater programming efforts than the circuit depicted in FIG. 4.

Although specific, preferred embodiments of the invention have been described, many variations and modifications will be apparent to those skilled in the art. The following claims are intended to cover all such variations and modifications.

What is claimed is:

1. A method for determining a heart rate from a signal having a plurality of frequency components at least one of which is indicative of heart beats, the method comprising the steps of:
    (a) processing said signal to produce first and second signals having different frequency characteristics;
    (b) identifying which of said first and second signals contains the more reliable, or higher quality, indication of said heart rate; and
    (c) generating a heart rate signal on the basis of the signal identified as containing the more reliable indication of said heart rate, said heart rate signal indicative of said heart rate.

2. The method recited in claim 1, wherein step (a) comprises processing said signal such that at least one of said first and second signals is indicative of an autocorrelation function.

3. The method recited in claim 2, further comprising detecting at least two peaks in said autocorrelation function and calculating said heart rate on the basis of the time interval between said peaks.

4. The method recited in claim 3, wherein said heart rate is calculated form beat to beat as the inverse of said time interval between said peaks.

5. The method recited in claim 2, wherein step (b) comprises computing a reliability coefficient as a function of the ratio of the amplitude of said autocorrelation function at two peaks.

6. The method recited in claim 2, wherein step (b) comprises computing a reliability coefficient as a function of the amplitude of the autocorrelation function at a peak.

7. The method recited in claim 1, wherein step (b) comprises:
    computing an autocorrelation function on the basis of at least one of said first and second signals;
    computing a cross-correlation function on the basis of at least said autocorrelation function; and
    identifying, on the basis of at least said cross-correlation function, which of said first and second signals contains the more reliable indication of said heart rate.

8. The method recited in claim 1, wherein step (b) comprises computing a reliability coefficient for said first and second signals and selecting, in discrete steps, the signal with the higher reliability coefficient.

9. The method recited in claim 8, wherein the selecting steps are performed when a predefined number of heartbeats have been detected.

10. The method recited in claim 8, wherein the selecting steps are performed at predefined time intervals.

11. The method recited in claim 1, wherein step (b) comprises computing a reliability coefficient for each of said first and second signals, and selecting the signal with the higher reliability coefficient when the reliability coefficients bear a predefined relation to each other.

12. The method recited in claim 1, wherein said first and second signals are produced by feeding a demodulated ultrasound signal to first and second filters, said first filter having low pass characteristics and said second filter having high pass characteristics.

13. The method recited in claim 12, wherein the first filter has an upper cutoff frequency and the second filter has a lower cutoff frequency, said upper and lower cutoff frequencies being approximately equal.

14. The method recited in claim 13, wherein said upper and lower cutoff frequencies are approximately 180 Hz.

15. The method recited in claim 12, wherein said ultrasound signal is an ultrasound burst signal.

16. A method for determining the heart rate of a fetus, comprising the steps of:
   (a) generating a high-frequency ultrasound signal;
   (b) irradiating said ultrasound signal into fetal tissue in the general direction of the fetal heart;
   (c) receiving an ultrasound signal reflected by the fetal tissue;
   (d) demodulating the received ultrasound signal;
   (e) feeding the demodulated ultrasound signal to at least two filters in parallel;
   (f) assessing the quality of the filtered signals;
   (g) selecting the filtered signal with the higher quality; and
   (h) producing a heart rate signal based upon the selected filtered signal, said heart rate signal indicative of the fetal heart rate.

17. An apparatus for determining a heart rate from a signal having a plurality of frequency components at least one of which is indicative of heart beats, comprising:
   (a) first and second processing means for processing said signal to produce first and second signals having different frequency characteristics;
   (b) selection means for identifying which of said first and second signals contains the more reliable, or higher quality, indication of said heart rate; and
   (c) third processing means for generating a heart rate signal on the basis of the signal identified as containing the more reliable indication of said heart rate, said heart rate signal indicative of said heart rate.

18. The apparatus recited in claim 17, wherein at least one of said first and second processing means comprises means for producing a signal that is indicative of an autocorrelation function.

19. The apparatus recited in claim 18, further comprising means for detecting at least two peaks in said autocorrelation function and means for calculating said heart rate on the basis of the time interval between said peaks.

20. The apparatus recited in claim 19, further comprising means for calculating said heart rate from beat to beat as the inverse of said time interval between said peaks.

21. The apparatus recited in claim 18, further comprising means for computing a reliability coefficient as a function of the ratio of the amplitude of said autocorrelation funciton at two peaks.

22. The apparatus recited in claim 18, further comprising means for computing a reliability coefficient as a function of the amplitude of said autocorrelation function at a peak.

23. The apparatus recited in claim 17, wherein said selection means comprises:
   means for computing an autocorrelation function on the basis of at least one of said first and second signals;
   means for computing a cross-correlation function on the basis of at least said autocorrelation function; and
   means for identifying, on the basis of at least said cross-correlation function, which of said first and second signals contains the more reliable indication of said heart rate.

24. The apparatus recited in claim 17, wherein said selection means comprises means for computing a reliability coefficient for said first and second signals and means for selecting the signal with the higher reliability coefficient, said selection performed in discrete steps.

25. The apparatus recited in claim 24, further comprising means for making the selection after a predefined number of heartbeats have been detected.

26. The apparatus recited in claim 24, further comprising means for making the selection at predefined time intervals.

27. The apparatus recited in claim 17, wherein said selection means comprises means for computing a reliability coefficient for each of said first and second signals, and means for selecting the signal with the higher reliability coefficient when the reliability coefficients bear a predefined relation to each other.

28. The apparatus recited in claim 17, said first and second processing means comprising first and second filter means for filtering said signal, said first filter means having low pass characteristics and said second filter means having high pass characteristics.

29. The apparatus recited in claim 28, wherein the first filter means has an upper cutoff frequency and the second filter means has a lower cutoff frequency, said upper and lower cutoff frequencies being approximately equal.

30. The apparatus recited in claim 29, wherein said upper and lower cutoff frequencies are approximately 180 Hz.

31. An apparatus for determining the heart rate of a fetus, comprising:
   (a) means for generating a high-frequency ultrasound signal;
   (b) means for irradiating said ultrasound signal into fetal tissue in the general direction of the fetal heart;
   (c) means for receiving an ultrasound signal reflected by the fetal tissue;
   (d) means for demodulating the received ultrasound signal;
   (e) means for feeding the demodulated ultrasound signal to at least two filters in parallel;
   (f) means for assessing the quality of the filtered signals;
   (g) means for selecting the filtered signal with the higher quality; and
   (h) means for generating a heart rate signal based upon the selected filtered signal, said heart rate signal indicative of the fetal heart rate.

32. An apparatus for monitoring a periodically-moving object, the apparatus having means for transmitting an ultrasound signal towards moving parts of the object and receiving a reflected signal, said apparatus characterized by:

means for filtering said complex signal to output filtered signals with different frequency characteristics;

means for enhancing periodic components of each filtered signal and suppressing non-periodic components of each filtered signal;

means for assessing the quality of each enhanced signal;

means for selecting a desired enhanced signal with the highest quality; and     means for calculating a rate of said periodic movement based upon said enhanced signal with the highest quality.

33. A method for monitoring a periodically-moving object, the method including transmitting an ultrasound signal towards moving parts of the object and receiving a reflected signal, said method characterized by the steps of:

filtering said complex signal to output filtered signals with different frequency characteristics;

enhancing periodic components of each filtered signal and suppressing non-periodic components of each filtered signal;

assessing the quality of each enhanced signal;

selecting a desired enhanced signal with the highest quality; and     calculating a rate of said periodic movement based upon said enhanced signal with the highest quality.

* * * * *